(12) United States Patent
Da Rocha Vaz Pato et al.

(10) Patent No.: US 9,980,684 B2
(45) Date of Patent: May 29, 2018

(54) STATIONARY SPECT IMAGING

(71) Applicant: MOLECUBES, Gent (BE)

(72) Inventors: Lara Da Rocha Vaz Pato, Coimbra (PT); Roel Van Holen, Melsen (BE); Stefaan Vandenberghe, Oosterzele (BE)

(73) Assignee: MOLECUBES, Ghent (BE)

( * ) Notice: Subject to any disclaimer, the term of this patent is extended or adjusted under 35 U.S.C. 154(b) by 0 days. days.

(21) Appl. No.: 15/328,399

(22) PCT Filed: Jul. 22, 2015

(86) PCT No.: PCT/EP2015/066710
§ 371 (c)(1),
(2) Date: Jan. 23, 2017

(87) PCT Pub. No.: WO2016/012476
PCT Pub. Date: Jan. 28, 2016

(65) Prior Publication Data
US 2017/0215822 A1    Aug. 3, 2017

(30) Foreign Application Priority Data
Jul. 22, 2014 (EP) ..................................... 14177918

(51) Int. Cl.
*A61B 6/06* (2006.01)
*A61B 6/03* (2006.01)
(Continued)

(52) U.S. Cl.
CPC ................ *A61B 6/06* (2013.01); *A61B 6/037* (2013.01); *G01T 1/2018* (2013.01); *G01T 1/249* (2013.01)

(58) Field of Classification Search
CPC ......... A61B 6/06; A61B 6/037; G01T 1/2018; G01T 1/249
See application file for complete search history.

(56) References Cited

U.S. PATENT DOCUMENTS

| | | | | |
|---|---|---|---|---|
| 7,521,681 | B2* | 4/2009 | Hawman | A61B 6/037 250/363.04 |
| 2009/0001273 | A1 | 1/2009 | Hawman | |
| 2009/0161819 | A1* | 6/2009 | Lewalter | A61B 6/032 378/16 |

FOREIGN PATENT DOCUMENTS

| | | |
|---|---|---|
| EP | 2414864 A1 | 2/2012 |
| WO | 2008007309 A1 | 1/2008 |

OTHER PUBLICATIONS

Anger, "Radioisotope Cameras," Instrumentation in Nuclear Medicine, G.J. Hine Ed., Chapter 19, 1967, pp. 485-552, vol. 1, Academic Press Inc., New York.
(Continued)

*Primary Examiner* — David Porta
*Assistant Examiner* — Faye Boosalis
(74) *Attorney, Agent, or Firm* — Workman Nydegger

(57) ABSTRACT

A collimator for a SPECT system, the collimator being adapted for absorbing and collimating gamma rays emitted by a radiation source within a field of view the collimator, said collimator having an alignment direction for directing along a longitudinal axis of a measuring cavity of the SPECT system and said collimator comprising at least one collimator body of radiation absorbing material, the collimator body comprising a plurality of apertures being formed in the collimator body, the plurality of apertures being arranged in a plurality of groups separated from each other in said alignment direction. The apertures of each group are oriented such as to define at least one projection view along a corresponding at least one projection direction. The plurality of said projection directions corresponding to each and every of said plurality of groups cover an angular range sufficiently large for sufficient image information for artifact-free reconstruction.

15 Claims, 6 Drawing Sheets

(51) Int. Cl.
*G01T 1/20* (2006.01)
*G01T 1/24* (2006.01)

(56) References Cited

OTHER PUBLICATIONS

Extended European Search Report for corresponding European Application No. 14177918.1, dated Jan. 28, 2015.
International Search Report for corresponding International PCT Application No. PCT/EP2015/066710, dated Oct. 5, 2015.

\* cited by examiner

STATIONARY SPECT IMAGING

FIELD OF THE INVENTION

The invention relates to the field of single photon emission computed tomography (SPECT). More specifically it relates to a collimator for a SPECT device, a SPECT device and a method for SPECT imaging.

BACKGROUND OF THE INVENTION

In Single Photon Emission Computed Tomography (SPECT), a nuclear imaging technique, molecules labeled with a gamma-emitting radioisotope, commonly referred to as a tracer, are injected into a biological entity under study, e.g. a patient. By measuring the gamma rays originating from the decaying isotope using a radiation detector, the distribution of the labeled molecule can be determined. The tracer spatial distribution can be reconstructed by determining the direction of incidence of the photons on the detector. In order to determine this direction of incidence, a collimator may be positioned in front of the radiation detector to select a spatial angle of incidence. Such collimator may consist of a block of material having a high attenuation coefficient with respect to the emitted gamma rays. In this material, small holes are provided to allow incidence of photons from a limited acceptance angle. In order to reconstruct a 3D image of the radioisotope distribution, each point in the distribution is observed from a sufficient number of angles, in order to achieve sampling completeness. In methods known in the art, this is usually achieved by rotating the collimator and detector around the subject. This rotation may for example be halted at certain angular positions to acquire data at these predetermined angles. However, the rotation of the system is never perfect due to mechanical tolerances, which leads to errors in the reconstruction due to the incorrect calibration of the system after rotation. The mechanism responsible for the rotation can also be quite large and expensive, e.g. due to the required high precision positioning of the gamma-cameras. Furthermore, while the system is rotating, it may not be available to acquire useful data for the reconstruction. Since the system typically has to be rotated such as to sample a large number of angles to get sufficient sampling, this implies an extended scanning period.

SPECT systems are known in the art which avoid rotation of at least the gamma camera detector or the collimator.

For example, the use of a rotating annular or cylindrical collimator in combination with a stationary detector system is known in the art. A similar approach is known in the art that uses slant-hole collimators, which are rotated around the scanner's longitudinal axis as well as around a perpendicular axis, while the detectors remain stationary. Such rotation of the collimators around an axis perpendicular to the longitudinal axis can be particularly challenging technically. Furthermore, even though the detector remains stationary in these systems known in the art, the collimator comprises a high attenuation material, which implies a high mass density, and therefore such system still requires a large and expensive actuation system to provide the precisely controlled rotation of the collimator.

The use of multi-head synthetic collimation is also known in the art. Such systems may use a radial motion of the detectors or multiple detectors arranged behind each other so as to provide a stacked detector acquisition. However, such systems have the disadvantage of requiring additional detectors and/or additional means for actuation of the detectors, thus increasing the size and cost of the system.

The use of multi-pinhole collimators to perform stationary cardiac SPECT is also known. In such systems, the collimator and the detector can be stationary. However, the imaging volume does not provide full 360 degree coverage in such systems, such that the useable field of view for accurate reconstruction is limited. Particularly, the useable field of view for accurate reconstruction, e.g. which satisfies sampling completeness, is relatively small compared to the volume delimited by the collimators. Therefore, a translation along three orthogonal axes of the bed on which the subject is positioned may be required.

For example, cylindrical multi-pinhole collimators are known in the art having one row of pinholes surrounding the subject. Such systems may be used in, for example, brain imaging and small-animal SPECT. However, the number of sampled angles obtained by such systems, and thus the different views of the object available for image reconstruction, is limited.

The use of another type of cylindrical multi-pinhole collimators surrounding the object is also known, in which the pinholes focus on a small field of view from sufficient viewing angles, e.g. for small-animal SPECT imaging. The subject may be translated on a bed along three orthogonal axes to obtain sufficient data from the region of interest. However, the application of such a system is limited by the use of pinholes, and full angular sampling of a large portion of the subject can only be achieved through bed translations along a non-linear path.

For example, EP 2414864 discloses an interwoven multi-aperture collimator, which comprises a body including a plurality of apertures in a two-dimensional grid. The two-dimensional grid is selectively divided into at least a first and a second group of apertures, defining corresponding views of an object to be imaged. The first group is formed by interleaving or alternating rows of the grid, and the second group is formed by the rows adjacent to the rows of the first group. Each aperture in the first group is arranged in a first orientation angle with respect to the surface plane of the collimator body, and each aperture in the second group is arranged in a second orientation angle with respect to the surface plane of the collimator body such that the apertures of the first group are interwoven with the apertures of the second group. This collimator was designed, however, to be attached to a single radiation detection module and to image the object from a single angular position, and so even if there are multiple aperture groups defining different views of the object the angular sampling of any particular part of the object is limited.

US2009/001273 discloses a collimator for a SPECT system. The collimator comprises a plurality of individual collimating segments. Each of the collimating segments are identical and comprise a plurality of apertures whereby each of the apertures have the same orientation angle with respect to the surface plane of the collimating segment. In US2009/001273 the individual collimating segments are angularly displaced from one another about a common central axis. As a result of this rotation each collimating segment defines a different projection view along a different projection direction. Such a collimator has the disadvantage that the different collimating segments need to be attached, leading to a loss of valuable detector space and a decreased image quality. Furthermore, in order to obtain sufficient angular sampling, parts of such a collimator are quite far from the detector and the object to be imaged, which leads not only to an inefficient use of space but to great losses in image quality.

SUMMARY OF THE INVENTION

It is an object of embodiments of the present invention to provide good and efficient means and methods for collimation in single-photon emission tomography (SPECT) imaging.

It is an advantage of embodiments of the present invention that SPECT imaging, e.g. 3D tomographic reconstruction of spatial gamma emission distributions, is enabled without requiring movement, e.g. neither translation nor rotation, of the collimator or the detector components of the SPECT scanner. Furthermore, it is an advantage of embodiments of the present invention that only a linear translation of the object to be imaged, e.g. along the longitudinal SPECT scanner axis, is required.

It is an advantage of embodiments of the present invention that a SPECT scanner system can have a simple mechanical design and can be operated by applying a simple scanning procedure. Embodiments of the present invention provide a high degree of mechanical stability in SPECT scanner systems, since no rotation or translation of the collimator is required. This implies a further advantage of avoiding errors caused by imperfections in the actuated movement of the collimator, which may be particularly critical due to the typically large mass of such collimators.

It is an advantage of embodiments of the present invention that a SPECT system can be manufactured and operated at low cost. For example, only a translation of a patient bed is required, which is provided by default in many SPECT systems known in the art for mounting and dismounting of the patient. This also means that the invention could even be mounted on existing SPECT scanners, thus avoiding the cost of producing a full system.

It is an advantage of embodiments of the present invention that a large field of view is available for tomographic reconstruction. It is an advantage of embodiments of the present invention that a sufficient angular sampling can be achieved for reconstructing the image without reconstruction artefacts. For example, at least 40 to 60 separate projections may be acquired over a range of 180 degrees around the scanner longitudinal axis. Furthermore, sampling of the object can be achieved evenly over 180 degrees, thus providing a uniform sampling of the full field of view.

It is an advantage of embodiments of the present invention that a transaxial field of view for reconstruction can extend close to the collimator, e.g. that sufficient sensitivity and angular sampling can be achieved for the points in a region close to the collimator. Thus, the volume enclosed by the collimator can be used in an efficient manner.

It is an advantage of embodiments of the present invention that a collimator and/or a SPECT device according to embodiments is simple to manufacture.

It is an advantage of embodiments of the present invention that no additional detector elements are required to obtain stationary imaging.

It is an advantage of embodiments of the present invention that full-body and organ imaging can be achieved in human or small-animal subjects.

It is an advantage of embodiments of the present invention that less detector space is lost.

It is an advantage of embodiments of the present invention that the shape of the at least one collimating block can closely match the shape of the detector.

It is an advantage of embodiments of the present invention that the shape of the at least one collimating block can closely match the shape of the measuring cavity of the object to be imaged.

It is an advantage of embodiments of the present invention that the apertures do not need to be cut off near the edges of the collimating body, independent of the shape of the apertures.

It is an advantage of embodiments of the present invention that a more compact collimator can be realized compared to prior art collimators.

It is an advantage of embodiments of the present invention that a more compact collimator can be realized in longitudinal direction, leading to a faster scanning procedure compared to prior art methods.

It is an advantage of embodiments of the present invention that the collimator results in less multiplexing artifacts compared to prior art collimators leading to an improved image quality.

It is an advantage of embodiments of the present invention that the collimator according to embodiments of the present invention is shorter in longitudinal direction compared to prior art collimators.

It is an advantage of embodiments of the present invention that the method for SPECT imaging according to embodiments of the present invention is faster compared to prior art methods.

It is an advantage of embodiments of the present invention that, compared to standard parallel-hole SPECT, the resolution improves towards the edges of the transaxial reconstruction field-of-view, with a corresponding decrease in sensitivity.

It is an advantage of embodiments of the present invention that the design of the collimator can allow to reconstruct a transaxial field of view of a larger portion of the collimator bore, using only patent bed translations along the longitudinal scanner axis.

Embodiments of the present invention advantageously may be used for full angular sampling of objects coming quite close to the collimator bore using only axial bed translations. The system thereby can be more compact and light than current stationary SPECT systems, have simple mechanics, are easy to calibrate and avoid rotation-related degradation of image quality as well as high maintenance costs. The systems also are especially suitable for applications with spatial restrictions, such as SPECT-MR inserts. The systems furthermore may be especially suitable for operating in continuous bed motion acquisition mode, as is used also in spiral CT and some PET applications.

Systems can be used for different practical applications, such as for example—but not limited to—for full-body imaging, brain imaging and small-animal imaging The above objective is accomplished by a method and device according to the present invention.

The present invention relates to a collimator for a SPECT system, the collimator being adapted for absorbing and collimating gamma rays emitted by a radiation source within a field of view of the collimator, said collimator having an alignment direction for directing along a longitudinal axis of a measuring cavity of the SPECT system, said collimator comprising at least one collimator body of radiation absorbing material, the collimator body comprising a plurality of apertures, the plurality of apertures being arranged in a plurality of groups separated from each other in said alignment direction, wherein the apertures of each group are oriented such as to define at least one projection view along a corresponding at least one projection direction, and wherein the plurality of said projection directions corresponding to each and every of said plurality of groups cover an angular range sufficiently large for sufficient image information for artifact-free reconstruction.

Where in embodiments of the present invention reference is made to a collimator body it is meant a continuous block of collimating material, e.g. radiation absorbing material. The continuous block advantageously may be a single piece material.

The projection view(s) of at least two different groups of apertures may correspond with views on different positions along the alignment direction.

The apertures of each group may be oriented so that each at least one projection direction is orthogonal to said alignment direction.

The plurality of groups may comprise rows of apertures, each row of apertures being aligned on a corresponding plane. The plane may be orthogonal to the alignment direction.

Each aperture within each group of apertures may be parallel to all other apertures in said group.

The apertures of each group may be oriented such as to define a number N larger than 1 of projection views along a corresponding number N of projection directions, each pair of said projection directions within the same group forming an angle being an integer multiple of 180/N degrees or 360/N degrees.

The plurality of apertures may comprise pinholes, parallel holes or fanbeam holes.

The holes may have the geometric shape of for example square prisms, truncated cones or truncates pyramids. The at least one projection view may comprise a parallel projection view or a diverging projection view.

The collimator may have a cross-section perpendicular to the alignment direction having a circular shape, an elliptical shape, an oval shape or a polygonal shape. The collimator may be fabricated of a radiation-absorbing material comprising a heavy metal or an alloy thereof.

The plurality of apertures may be obtained by a metal additive manufacturing technique.

The collimator may be adapted in shape to fit between an at least one detector module and the measuring cavity of the SPECT system.

The present invention also relates to a SPECT system comprising a measuring cavity having a longitudinal axis, a collimator as described above having its alignment direction aligned to said longitudinal axis, a radiation detection means adapted for receiving radiation passing through the collimator and for outputting a signal representative of the received radiation as function of spatial position, and an actuation means for translating a radiation source through said measuring cavity along the longitudinal axis while imaging the radiation source.

The collimator and said radiation detection means may be mechanically connected to a frame for maintaining said collimator and said radiation detection means stationary while imaging the radiation source.

The present invention also relates to a method for SPECT imaging, the method comprising providing a radiation source, collimating gamma rays emitted by the radiation source, said collimating being performed in a plurality of spatial regions arranged in a plurality of groups, each group being separated from each other group in the direction of a longitudinal axis, said collimation in the spatial regions of each group defining at least one projection view along a corresponding at least one projection direction, the or each at least one projection direction being orthogonal to said alignment direction, wherein the plurality of said projection directions corresponding to each and every of said plurality of groups cover an angular range sufficiently large for sufficient image information for artifact-free reconstruction, for example cover an angular range of at least 180 degrees at angular intervals, acquiring imaging information corresponding to said plurality of views, and translating the radiation source in the longitudinal direction in order to acquire said imaging information corresponding to said plurality of views such that each view collects gamma rays emitted by a different volume within the radiation source.

The method may comprise obtaining an estimation of the 3D spatial distribution of the radiation source by applying a reconstruction algorithm to the acquired imaging information, using an accurate model of the SPECT system acquisition.

The method advantageously may make use of a collimator as described above. In view of the compactness of the collimator, the amount of translation required in the longitudinal direction can be limited.

The present invention furthermore relates to the use of a SPECT system as described above for imaging a gamma-radiation emitting object.

Particular and preferred aspects of the invention are set out in the accompanying independent and dependent claims. Features from the dependent claims may be combined with features of the independent claims and with features of other dependent claims as appropriate and not merely as explicitly set out in the claims.

These and other aspects of the invention will be apparent from and elucidated with reference to the embodiment(s) described hereinafter.

Figure 1:
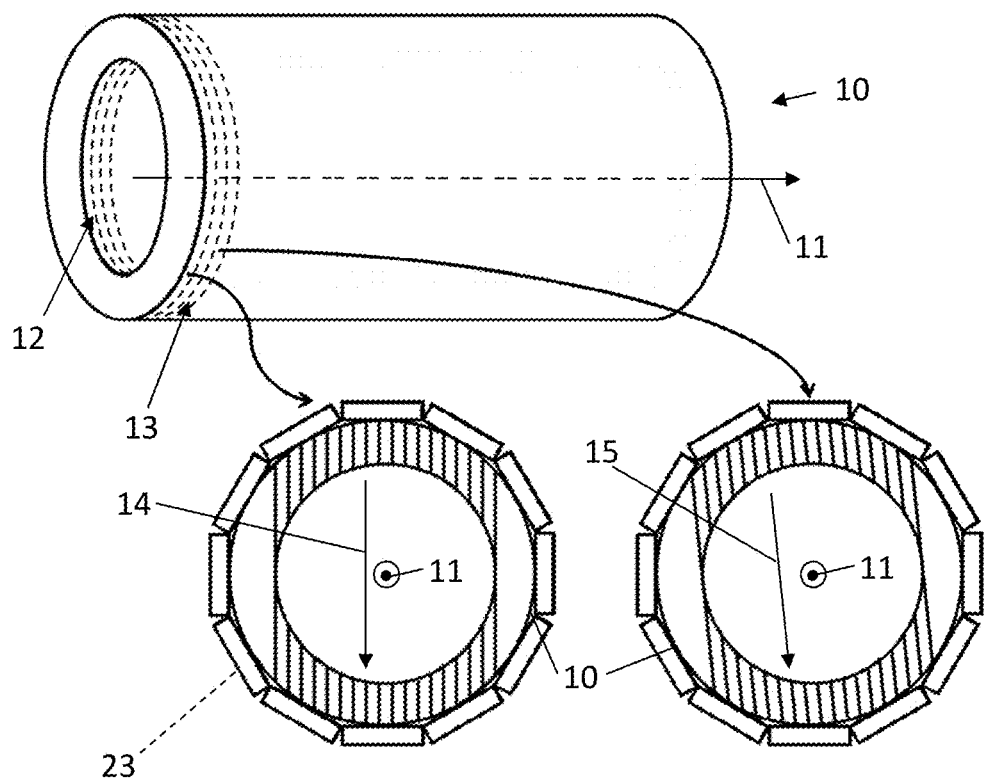
FIG. 1 shows a collimator according to a first exemplary embodiment of the present invention.

The drawings are only schematic and are non-limiting. In the drawings, the size of some of the elements may be exaggerated and not drawn on scale for illustrative purposes.

Any reference signs in the claims shall not be construed as limiting the scope.

In the different drawings, the same reference signs refer to the same or analogous elements.

DETAILED DESCRIPTION OF ILLUSTRATIVE EMBODIMENTS

The present invention will be described with respect to particular embodiments and with reference to certain drawings but the invention is not limited thereto but only by the claims. The drawings described are only schematic and are non-limiting. In the drawings, the size of some of the elements may be exaggerated and not drawn to scale for illustrative purposes. The dimensions and the relative dimensions do not correspond to actual reductions to practice of the invention.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

Moreover, the terms top, under and the like in the description and the claims are used for descriptive purposes and not necessarily for describing relative positions. It is to be understood that the terms so used are interchangeable under appropriate circumstances and that the embodiments of the invention described herein are capable of operation in other orientations than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

In the description provided herein, numerous specific details are set forth. However, it is understood that embodiments of the invention may be practiced without these specific details. In other instances, well-known methods, structures and techniques have not been shown in detail in order not to obscure an understanding of this description.

Where in embodiments of the present invention reference is made to "a bed", reference equally can be made to "a couch".

In a first aspect, the present invention relates to a collimator for a SPECT system. This collimator is adapted for absorbing and collimating gamma rays emitted by a radiation source within the field of view of the collimator. The collimator furthermore has an alignment direction which typically may correspond with a longitudinal axis of a measuring cavity of the SPECT system. The collimator comprises at least one collimating body. The collimating body or one of the collimating bodies comprises a continuous block of collimating material wherein a plurality of apertures is formed, the plurality of apertures being substantially arranged in a plurality of groups separated from each other in the alignment direction. The apertures of each group are oriented such as to define at least one projection view along a corresponding at least one projection direction. At least some different groups of apertures thereby may define a projection view at different positions along the alignment direction. In some embodiments, one, more or all of the groups may provide at least one projection direction being orthogonal to the alignment direction. Furthermore, the plurality of the projection directions corresponding to the ensemble of groups cover an angular range sufficiently large to obtain sufficient information from the object, e.g. an angular range of at least 180 degrees, e.g. at angular intervals of e.g. 5 degrees or less, e.g. 3 degrees or less, e.g. 2 degrees, or even less, such as 1 degree or 0.5 degrees.

The collimator according to embodiments of the present invention may comprise one or more collimating bodies of collimating material. The collimators shown in FIG. 1-FIG. 4 are made of one collimating body/block of collimating material. The collimating body/block comprises a plurality of apertures arranged in a plurality of groups separated from each other in the alignment direction. Alternatively, the collimator according to embodiments of the present invention may be made of several collimating bodies, each of the collimating bodies being made of collimating material and each of the collimating bodies comprising a plurality of apertures being substantially arranged in a plurality of groups separated from each other in the alignment direction. As an example, without being limited thereto, the collimator shown in FIG. 6 may be made of 3 collimating bodies, one of the collimating bodies being shown in FIG. 7. The one or more collimating bodies may be arranged to form a hollow cavity, the measuring cavity, of a predetermined thickness.

In some embodiments, the groups of apertures are arranged such that each group of apertures comprises apertures being arranged in a same plane. Nevertheless, the present invention also relates to embodiments wherein the plurality of apertures is arranged differently. For example, the apertures may be arranged in a helical configuration of apertures with a sufficiently small pitch such that groups can be defined that the apertures of one group still substantially corresponds with a same plane or slice.

Referring to FIG. 1, a collimator 10 according to a first exemplary embodiment of the present invention is shown. This collimator is adapted for use in a single-photon emission computed tomography (SPECT) system 20, e.g. as shown in the transaxial illustration in FIG. 2. The collimator has an alignment direction 11 corresponding with a longitudinal axis 21 of a measuring cavity 22 of the SPECT system 20, e.g. an axial axis of the measuring cavity. This longitudinal axis 21 may be for example a symmetry axis of the measuring cavity. The longitudinal axis 21 may be a longitudinal axis defining a direction for translating a radiation source to be imaged through the measuring cavity during imaging. The SPECT system 20 may comprise detection means, e.g. at least one detector module 23, e.g. a gamma radiation detector comprising a scintillator crystal and a patient bed 24 for positioning a patient 25 in the measuring cavity 22. The detection means may, when viewed from the cavity, be arranged behind the collimator for receiving, in a position-related manner, the radiation emitted within the measuring cavity. The detection means may be electronically or optically readable, e.g. may be adapted to output an optical or electrical signal representative of the position-related received radiation.

Figure 2:
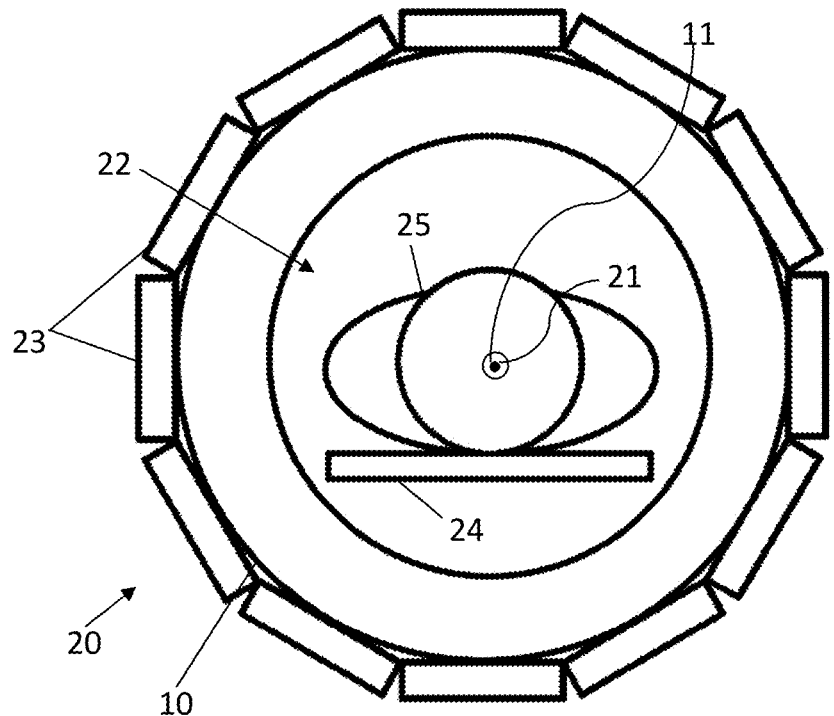
FIG. 2 shows a SPECT system according to embodiments of the present invention.
Figure 3:
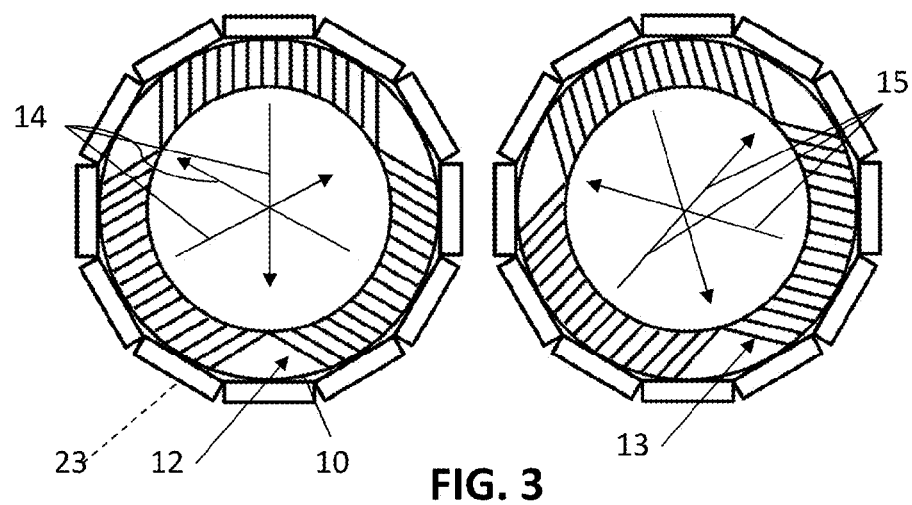
FIG. 3 shows a collimator according to a second exemplary embodiment of the present invention.
Figure 4:
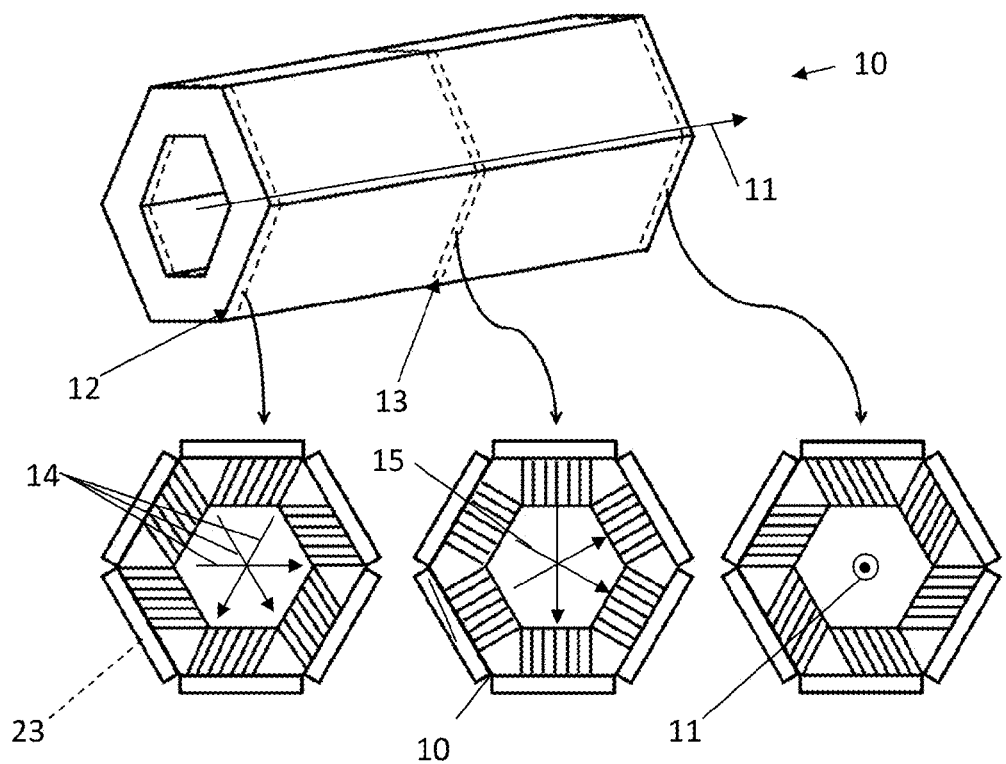
FIG. 4 shows a collimator according to a third exemplary embodiment of the present invention.
Figure 6:
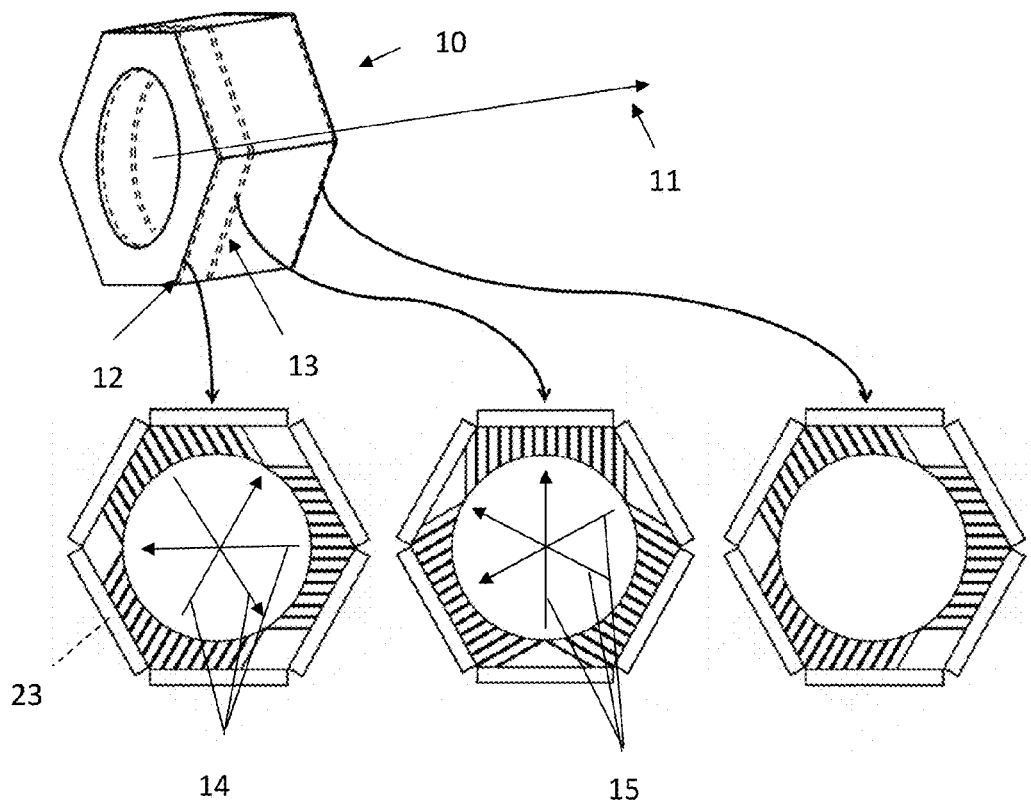
FIG. 6 shows a collimator according to a fourth exemplary embodiment of the present invention.
Figure 7:
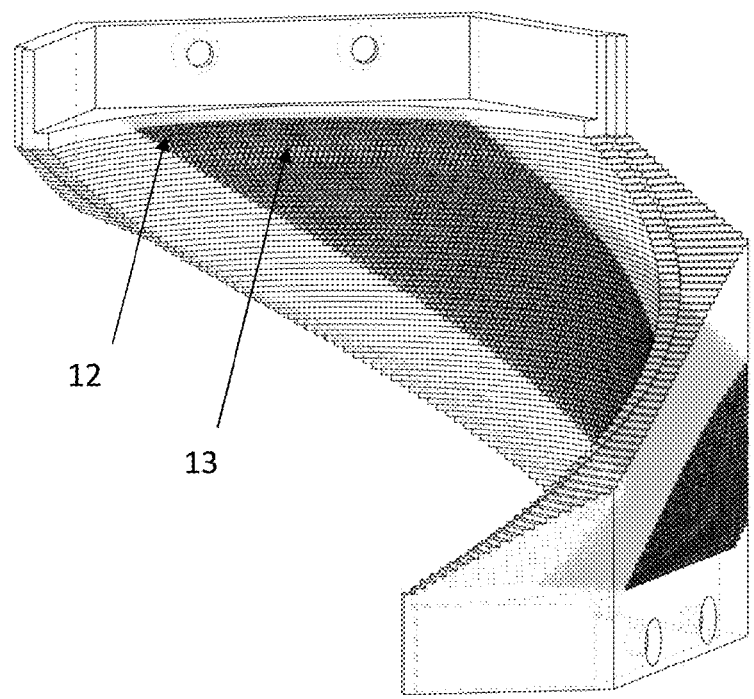
FIG. 7 shows a collimating body of a collimator according to the fourth exemplary embodiment of the present invention.

The collimator 10 may be adapted in shape to fit between the at least one detector module 23 and/or the measuring cavity 22. For example, the collimator may be adapted for at least partially surrounding the measuring cavity, e.g. to at least partially define a cavity wall of the measuring cavity. The collimator may be a multi-view collimator suitable for stationary tomographic gamma ray imaging, e.g. for use in a SPECT system 20 which does not require movement of the collimator or of a gamma detector. In embodiments according to the present invention, the collimator may have the shape of a hollow cylinder of a predetermined thickness. However, a cross-section of the collimator perpendicular to the alignment direction may have any suitable shape, e.g. a circular shape, an elliptical shape, an oval shape or a polygonal shape. A cross section of the inner face of a collimator perpendicular to the alignment direction may have a shape adapted to the shape of the measuring cavity. Such a cross section may for instance have a circular shape as shown in FIG. 1-FIG. 3 and FIG. 6 or a polygonal shape as shown in FIG. 4. A cross section of the outer face of a collimator perpendicular to the alignment direction may have a shape adapted to the shape of the detector module. Such a cross section may for instance have a circular shape as shown in FIG. 1-FIG. 3 or a polygonal shape as shown in FIG. 4 and FIG. 6.

It is an advantage of a collimator according to embodiments of the present invention that it is suitable for use in a stationary SPECT system, e.g. a SPECT system which does not require translation or rotation of the collimator. Therefore, where a rotating collimator requires a shape adapted for allowing this rotation, so as to rotate unobstructed, a collimator according to embodiments of the present invention can have a shape that conforms more closely to the cross-sectional shape of the object being imaged, for example an elliptical cross-section having a minor axis, e.g. a conjugate diameter, of less than the transaxial width of the object being imaged, but more than the transaxial height of the object.

The collimator 10 is adapted for absorbing and collimating gamma rays emitted by a radiation source within the field of view of the collimator. For example, the collimator 10 may be adapted to selectively absorb gamma radiation emitted by a radiation source, e.g. the patient 25, positioned in the measuring cavity 22 such as to collimate this gamma radiation onto the at least one detector module 23, when the collimator 10 is installed in the SPECT system 20. The collimator comprises at least one collimator body adapted for absorbing and collimating gamma rays emitted by the radiation source within the field of view of the collimator, e.g. when this radiation source is translated through the measuring cavity of the SPECT system along the longitudinal axis. The collimator body may have a first major surface for directing toward the radiation source, e.g. for disposing closest to the radiation source in the SPECT system, and a second major surface, opposite the first major surface, for directing toward the at least one detector module 23.

The collimator, e.g. the at least one collimator body, may be fabricated of a radiation-absorbing material, for example a radiation-absorbing material having a high mass density and a high atomic mass. For example, the radiation-absorbing material may be selected based on the type of incident radiation and the energy of the radiation when it strikes the first major surface of the collimator. The collimator may be adapted for, for example, absorbing radiation emitted by a radioisotope such as $^{125}$I, $^{111}$In, $^{99m}$Tc or $^{103}$Pd. The radiation-absorbing material may for example comprise a heavy metal such as lead (Pb), tungsten (W), tantalum (Ta), iridium (Ir), platinum (Pt), gold (Au), molybdenum (Mo), copper (Cu) or an alloy comprising at least one of these heavy metals.

A plurality of apertures is formed in one of the at least one collimating body. For example, the apertures may traverse the collimator body from the first major surface to the second major surface, such as to allow radiation from within the field of view, e.g. from a radiation source in the measuring cavity, to reach the at least one radiation detector module in a predetermined region, e.g. a pixel element of the detector, along a predetermined direction while blocking such radiation along other directions.

In embodiments according to the present invention, the plurality of apertures may comprise for example pinholes, parallel holes or fanbeam holes. The apertures may for example have the shape of a truncated cone, a truncated pyramid, a cylinder or a prism. For example, in a collimator according to embodiments, the apertures may have a geometric cross-section defined by at least one of a circle, a parallelogram, a rectangle, a square, a hexagon or a polygon. Thus, the apertures may comprise parallel collimator holes, fanbeam collimation holes or pinholes.

In a collimator according to embodiments of the present invention, the plurality of apertures may be formed by machining holes in the collimator, e.g. in the collimator body, by laterally arranging septa so as to form radiation-guiding conduits or channels, and/or by vertically stacking multiple layers of radiation-absorbing materials with each layer having a predetermined aperture cross-section. For example, the apertures may be provided in the collimator by applying an additive manufacturing technique. Since a collimator according to embodiments of the present invention may be difficult to manufacture with traditional manufacturing techniques, e.g. by molding or milling, metal/material additive manufacturing (3D printing) methods may offer an advantageous alternative.

The plurality of apertures of the collimating body is arranged in a plurality of groups 12, 13 separated relative to each other in the alignment direction 11. For example, the plurality of apertures may be partitioned, e.g. may be partitionable, into the plurality of groups by a set of planes orthogonal to the alignment direction 11. The plurality of groups may be rows of apertures, e.g. each group comprising one row of apertures aligned on a corresponding plane orthogonal to the alignment direction 11, or each group may comprise more than one such row, forming a block of adjacent rows. In such block of adjacent rows, the apertures may be arranged in a rectangular grid, e.g. in a rectilinear grid curved over the plane of the first major surface, which may be curved, e.g. a cylindrical surface as shown in FIG. 1, or piecewise flat, e.g. forming a triangular, hexagonal or other polygonal prism.

In a collimator according to embodiments of the present invention, one group of apertures comprises only one row of collimator apertures. Such embodiments allow to have only one row of collimator apertures per sampling angle, i.e. to have apertures sampling in a different direction on different positions along the alignment direction of the collimator, i.e. on different positions along the longitudinal direction of a SPECT system comprising such a collimator. Such embodiments of the present invention have the advantage of offering a very compact collimator, i.e. for instance having reduced dimensions in the longitudinal direction compared to prior art systems such as US2009/001273 where it would be very inefficient to have only one row of apertures per collimating segment since a large proportion of the collimator would then comprise gaps between the segments.

For example, the apertures may be at least substantially arranged in a plurality of flat planes which planes are at least substantial parallel to each other and separated in the direction of the longitudinal axis relative to each other. The distance between neighbouring planes in such plurality of flat planes may be smaller or larger than the distance between neighbouring apertures within any of such planes.

The apertures of each group 12, 13 are oriented such as to define at least one projection view along a corresponding at least one projection direction 14, 15, each projection direction being orthogonal to the alignment direction 11. Thus, the apertures of each group, e.g. respectively group 12 and group 13, may be oriented such as to allow gamma radiation to pass through the collimator body along a collimation direction, e.g. respectively direction 14 and direction 15, defining a parallel projection view, as shown in FIG. 1. However, in embodiments of the present invention, the apertures of each group 12, 13 may be oriented such as to define a plurality of projection views along a corresponding plurality of projection directions 14, 15, wherein each projection direction is orthogonal to the alignment direction 11.

FIG. 3, FIG. 4 and FIG. 6 illustrate other exemplary embodiments wherein each group comprises apertures oriented such as to define three parallel projection views, e.g. at 60° angles with respect to each other. Thus, in these embodiments of the present invention, the apertures of each group may be oriented such as to define a number N>1 of projection views along a corresponding number N of projection directions (14,15), each pair of said projection directions within the same group forming an angle being an integer multiple of 180/N degrees or 360/N degrees. Although such embodiments provide an efficient sampling of projection directions, embodiments of the present invention are not necessarily limited thereto, e.g. a number of projection views per group may be spaced at angular intervals which do not relate to each other as a sequence of integer multiples. Such arrangement may for example be optimized for a particular shape, mass density distribution and/or gamma emitter concentration distribution of the object to be imaged, or of a generalized prototype abstraction of the object.

Furthermore, the at least one projection view may refer to a parallel projection view, but may also refer to a converging or diverging projection view, e.g. a fanbeam projection view. While in the case of a parallel projection, the at least one projection direction corresponds to the collimation direction of each aperture contributing to this parallel projection view, in the case of a converging or diverging projection view, the at least one projection direction refers to a central line of sight axis of the projection.

Furthermore, the plurality of the projection directions 14,15 corresponding to each and every group 12,13 of the plurality of groups cover an angular range of at least 180 degrees at angular intervals of e.g. 5 degrees or less, e.g. 3 degrees or less, e.g. 2 degrees, or even less, such as 1 degree or 0.5 degrees.

Even though for the sake of clarity only two groups 12, 13 are illustrated in FIG. 1, it is to be understood that the plurality of apertures formed in the collimator 10 are arranged in a larger number of groups, for example at least 60 groups when the apertures of each group are oriented to define a single projection view along a single projection direction as illustrated in FIG. 1. The set of projection directions collected over all groups, e.g. the set of 60 projection directions in the example hereinabove, have an associated set of angles relative to a basis vector in a plane orthogonal to the alignment direction 11, e.g. relative to a first projection direction 14 in a first group 12 of the plurality of groups, which covers at least 180 degrees at angular intervals. For example, the exemplary set of angles may consist of angular values from 0° to 180° in 3° increments, thus forming 60 groups.

Thus, the at least one projection direction of each group may differ from the at least one projection direction of each other group by an offset angle in a plane orthogonal to the alignment axis such that the plurality of offset angles covers an angle of at least 180° around the alignment axis at angular intervals of e.g. 3°.

In a first exemplary embodiment, shown in FIG. 1, the collimator may be a hollow cylinder of a predetermined thickness, for placing in a SPECT system such as to be surrounded with radiation detectors. However, the shape of the collimator may also be different, e.g. a cross-section of the collimator perpendicular to the alignment direction may have an elliptical shape, an oval shape or a polygonal shape. The apertures may be grouped in different rows, as shown in FIG. 1, with the row number incrementing along the alignment direction 11, thus along the longitudinal scanner axis when installed in the SPECT system. The apertures, e.g. the collimator holes, may all lie in transverse planes, oriented perpendicular to the longitudinal axis. Within each group of apertures, e.g. within each row, each aperture may be parallel to all others. Each row of apertures may thus define only a single view, e.g. all holes may be oriented parallel to each other in the transverse plane.

Within each subsequent row, collimator apertures may collimate the radiation at a different incremental angle, thus defining a different view of the object being imaged for each aperture row. In such an arrangement according to embodiments of the present invention, complete angular sampling can be achieved by stepping or translating the patient through the SPECT system, e.g. through the measuring cavity along the longitudinal axis, since the number of rows of apertures provided is sufficient to cover a sufficient angular span of views, e.g. at least 180°, for example substantially 360°. For example, the collimator may comprise 60 rows, each row comprising apertures oriented at a 3 degree increment in viewing angle relative to the orientation of the apertures in a previous row. The radiation source, e.g. the patient, may be stepped through the collimator in 60 steps along the longitudinal direction with an incremental translation equal to the collimator row pitch. In this way, complete angular sampling of the radiation source, i.e. 60 views per transaxial slice, is achieved by a linear translation, e.g. a stepwise movement of the source along a straight line. Even though the collimation scheme may render the reconstruction problem more complex with respect to prior art methods, the collimator physics can be modeled according to methods known in the art, such that the skilled person can determine a suitable iterative reconstruction technique without exercising an inventive effort.

A collimator according to embodiments of the present invention, for example the exemplary embodiments illustrated in FIG. 4 and FIG. 6, may have a shape adapted for fitting inside a hexagonal set of detectors. Such collimator may have the shape of a hollow hexagonal prism having a predetermined thickness, for placing in a SPECT system such as to be surrounded with radiation detectors. However, the shape of the collimator may also be different, e.g. a cross-section of the collimator perpendicular to the alignment direction may have an elliptical shape, an oval shape or a polygonal shape.

In the exemplary embodiment shown in FIG. 4, the apertures, e.g. the collimator holes, may have the shape of square prisms, e.g. tilted square prisms, which may lie in transverse planes, oriented perpendicular to the longitudinal axis. On the inner part of the collimator, the apertures may be spaced at regular intervals, spanning the total 360°. Each transverse slice containing one row of holes may be divided into six sectors, one for each side of the hexagon, and within each sector the holes may be parallel to each other such that three views are defined. From one transaxial slice to the next, the radial axis of the holes may be rotated by a small angle around the base of the prism which is closer to the field of view, such as to be directed at the field of view from a different direction. When taking all the rows into account, each sector spans a total of 60°, and the six sectors span 360°, but the holes are not always looking at the same region in space. A collimator according to embodiments may also have a similar geometry constructed for other prismatic collimator shapes, such as a triangular prism, which can be divided into three sectors, in order to use the detector geometry most efficiently.

In embodiments of the collimator according to the present invention the shape and/or the length and/or the size of apertures, for instance the diameter of the apertures, belonging to one or more different groups may differ. Such embodiments may allow to vary the sensitivity and resolution of a particular region in the field of view.

In the exemplary embodiment shown in FIG. 6, each transverse slice containing one row of holes may be divided into 3 sectors. From one transaxial slice to the next, the radial axis of the holes may be rotated by a small angle around the central axis of the collimator. Such an embodiment results in a larger field of view compared to the embodiment shown in FIG. 4.

In embodiments of the collimator according to the present invention the apertures of one group are rotated with a certain angle with respect to the apertures belonging to a subsequent group. However, contrary to prior art systems where the apertures belonging to different groups are angularly displaced with respect to each other by rotating the different collimating blocks/bodies/segments, the apertures themselves are rotated in embodiments according to present invention and the collimating block comprising the plurality of groups of apertures stays stationary. Such embodiments allow to closely match the shape of the collimator and the collimator body to the schape of the detector and/or to the shape of the measuring cavity. As a result, the collimator according to embodiments of the present invention may be positioned closer to the detector and/or to the object to be imaged, resulting in a more compact and cheaper system, as well as in an improved image quality.

In embodiments of the collimator according to the present invention, the apertures of one group are rotated with a certain angle with respect to the apertures belonging to a subsequent group. The rotation may be for instance performed about the central axis of the collimator. When integrating the collimator in a SPECT system, the central axis of the collimator may coincide with the central longitudinal axis of the SPECT system. Such embodiments have the advantage that a sampling similar to that of an actual rotating SPECT system is replicated, which results in a larger field of view compared to prior art collimators. The rotation may for instance be performed about an axis located at the intersection of the apertures with an inner face of the collimator such as for instance shown in FIG. 4.

In a second aspect, the present invention relates to a SPECT system comprising a collimator according to embodiments of the first aspect of the present invention. Referring to FIG. 2, an exemplary SPECT system 20 according to embodiments of the invention is illustrated. The SPECT system comprises a measuring cavity 22 having a longitudinal axis 21, and a collimator 10 according to embodiments of the invention, as discussed hereinabove, aligned to this longitudinal axis 21, e.g. such that an alignment direction 11 of the collimator corresponds with the longitudinal axis 21. The SPECT system further comprises an actuation means 24 for translating a radiation source, e.g. a patient 25 having radioisotopes injected into his body, along the longitudinal axis while imaging the radiation source. The SPECT system 20 also comprises radiation detection means 23, e.g. at least one detector module, e.g. a gamma radiation detector such as a scintillation detector. The radiation detection means 24 may be adapted for receiving radiation passing through the collimator and for outputting a signal representative of the received radiation as function of spatial position.

While stationary SPECT systems known in the art may be based on multi-pinhole collimation, which may provide complete angular sampling but only for a field of view which is small in relation to the volume circumscribed by the collimator, a system according to embodiments of the present invention may use a wide variety of collimation methods, e.g. tilted parallel-holes, whose direction varies as function of the axial position. A complete angular sampling can thus be achieved over a larger fraction of the volume circumscribed by the collimator. Furthermore, only longitudinal bed translations are required during image acquisition, and a high volume-sensitivity can be achieved.

Figure 5:
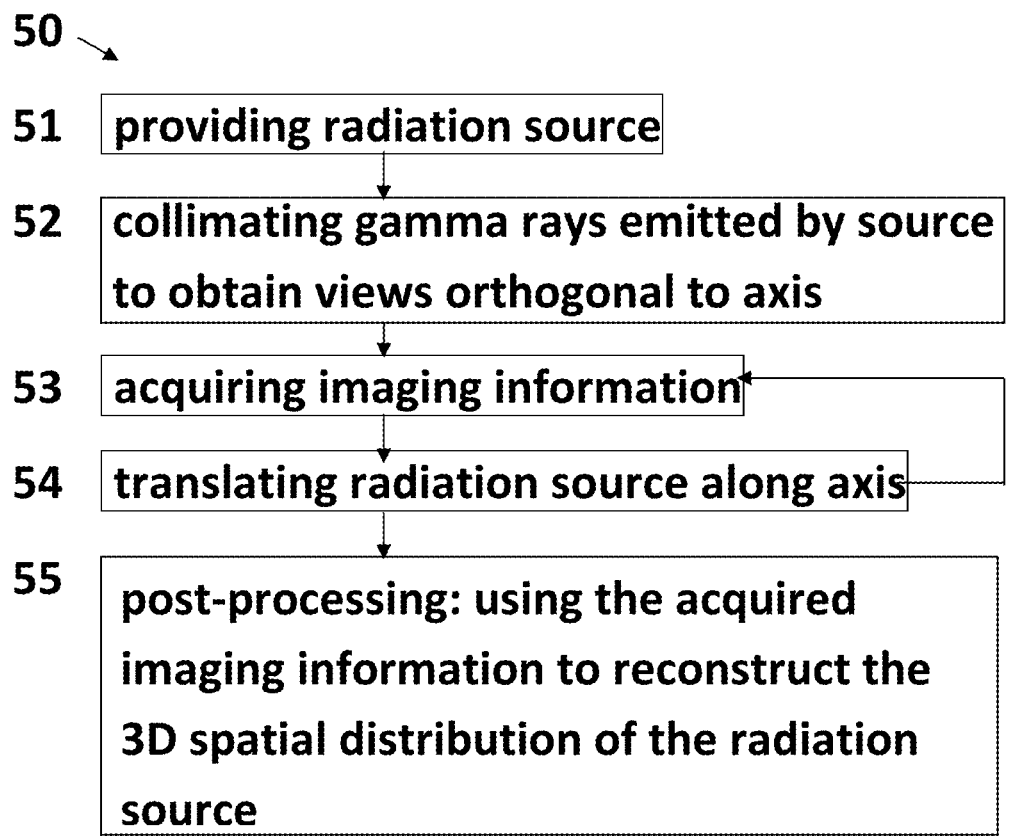
FIG. 5 illustrates a method according to embodiments of the present invention.

In a third aspect, the present invention relates to a method for SPECT imaging of a radiation source. Referring to FIG. 5, a method 50 according to embodiments of the present invention is shown. The method 50 comprises providing 51 a radiation source, e.g. an object comprising a distribution of radio-isotopes emitting gamma radiation, for example a human or animal subject pre-injected with radioisotopes. The method further comprises absorbing and collimating 52 gamma rays emitted by the radiation source. This collimation is performed in a plurality of spatial regions arranged in a plurality of groups 12, 13. Each such group is separated from each other group in the direction of a longitudinal axis 21.

The collimation in the spatial regions of each group defines at least one projection view along a corresponding at least one projection direction 14, 15. Advantageously, the projection views are at different positions along the alignment direction. The or each at least one projection direction may be orthogonal to the alignment direction 11. The plurality of the projection directions 14,15 corresponding to each and every one of the plurality of groups 12,13 cover an angular range of at least 180 degrees at angular intervals of e.g. 5 degrees or less, e.g. relative to a constant basis vector lying within a plane orthogonal to the alignment direction.

The method further comprises acquiring 53 imaging information corresponding to said plurality of views.

The method 50 also comprises translating 54 the radiation source in the longitudinal direction in order to acquire the imaging information corresponding to the plurality of views such that each view collects gamma rays emitted by a different volume within the radiation source. The method 50 additionally may comprise a post-processing phase 55, in which a reconstruction algorithm is applied to the acquired imaging information in order to obtain an estimation of the 3D spatial distribution of the radiation source. Advantageously, the model of the SPECT system acquisition taken into account is as accurate as possible.

The method 50 according to embodiments of the present invention may make use of a collimator according to embodiments of the present invention. It thereby is an advantage that the collimator can be very compact, such that the amount of translation required in longitudinal direction can be short.

In an example demonstrating aspects of the present invention, the invention not being intended to be limited by the example provided, Monte Carlo simulations were performed of a system according to the embodiment shown in FIG. 4. The simulations used a collimator geometry according to embodiments, designed for a target-resolution of 4 mm at the center of the measuring volume in order to image a uniform phantom and a resolution phantom with the approximate size of a rat. The projection data was reconstructed using the Maximum-Likelihood Expectation-Maximization algorithm. The reconstructions showed that this SPECT configuration according to embodiments can be used to image objects with a diameter of about 75% of the collimator diameter with a resolution after reconstruction of about 3 mm. The results confirmed that such a collimator geometry can be applied to obtain artefact-free reconstruction.

In another example demonstrating aspects of the present invention, a SPECT system (collimator and detectors) comprising a collimator as shown in FIG. 6 was designed to image a volume of 65 mm diameter (the size of a rat) with a set of six 49 mm×49 mm detectors, with a target resolution at the center of the system of 2 mm. Realistic data acquisition was simulated using Monte Carlo-based software. The obtained projection data was reconstructed using the Maximum-Likelihood Expectation-Maximization algorithm, with an accurate analytical model of the projection and back-projection. The predicted average sensitivity of the system (detector efficiency included) over the reconstruction field of view was about 148 cps/MBq, and the resolution after reconstruction ranged between 1 and 1.6 mm. The scanning of uniform and resolution phantoms of 65 mm diameter, using only longitudinal bed movement, was simulated, and the reconstructed images showed no artifacts, which indicates a useable transaxial field of view of at least 75% of the area confined by the collimator. A whole-body rat scan was also simulated under realistic experimental conditions, showing the feasibility of using the designed system for pre-clinical purposes.

In another example demonstrating aspects of the present invention, three SPECT systems comprising a collimator as shown in FIG. 3 were simulated for imaging of the full human body, the human brain and mice, respectively. The target central resolution considered was about 13 mm, 6 mm and 1 mm, respectively. Preliminary results using realistic injected activities and scanning times show artifact-free images and which could be used for clinical/pre-clinical purposes, once again showing the possibility of using the proposed invention for relevant applications.

Three possible designs (for different imaging scales) for full-body, brain and small-animal imaging respectively are described and their feasibility is tested using simulations. The system modelling method was validated against realistic Monte Carlo simulations, and the systems' performances and reconstructions were evaluated.

Figure 8:
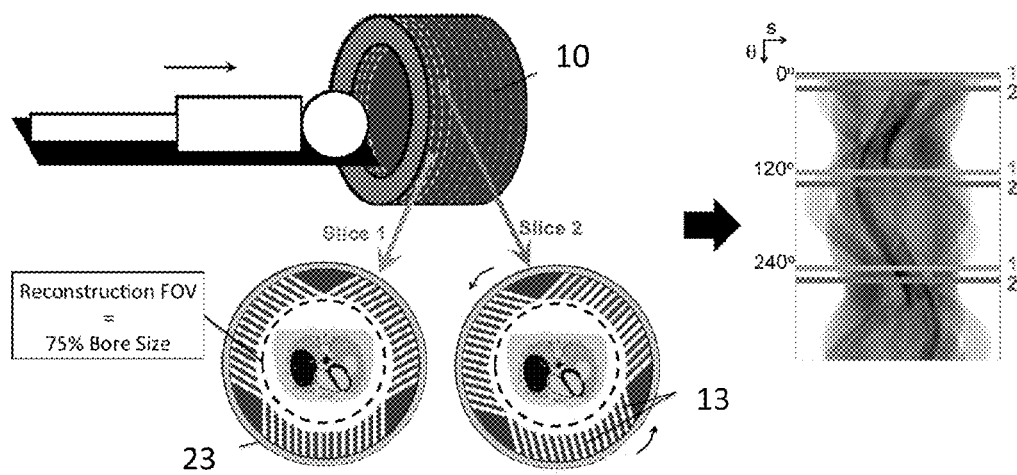
FIG. 8 shows an exemplary collimator design according to an embodiment of the present invention.
Figure 9:
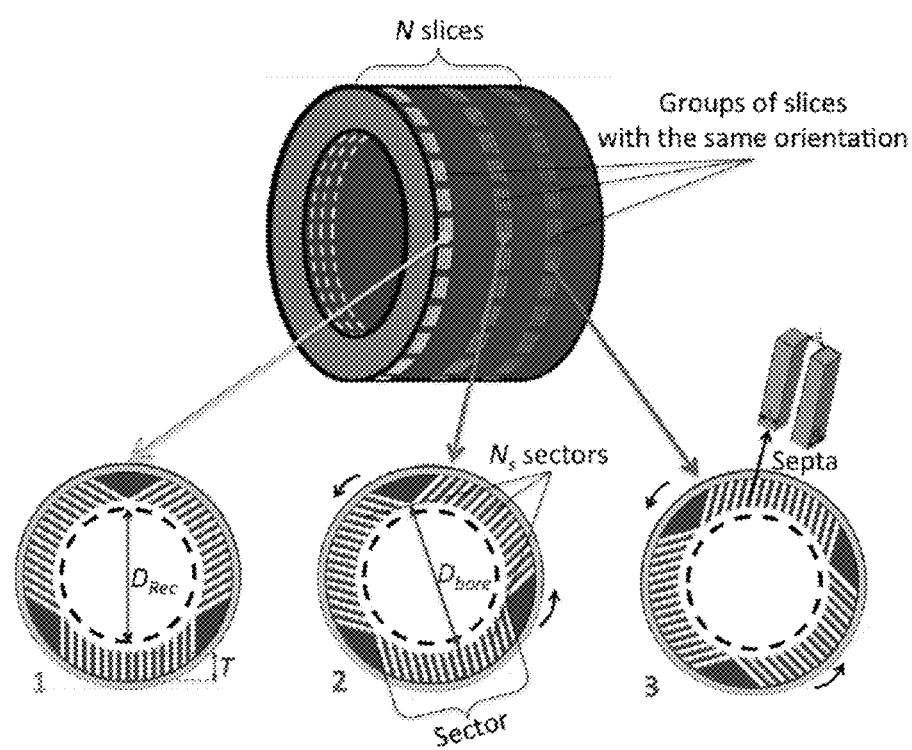
FIG. 9 a collimator design according to an embodiment of the present invention.

As shown in FIG. 8, the collimators had a cylindrical shape and each transaxial slice had three sectors of parallel holes, which gives us a reconstruction FOV of 75% of the total transaxial area inside the collimator bore. The collimator material used was tungsten, and each aperture hole could be obtained by removing an identical square prism from the main body (FIG. 9). The detectors were continuous NaI crystals, of cylindrical shape, with an inner diameter and height equal to the outer shape of the collimator.

The parameters of the three different systems are shown in the table below, and some of the parameters are represented in FIG. 9. In this table only d, t, RD and the parameters with an integer value are exact, the others have been rounded for this table but their exact values are set by the system geometry. The penetration and resolution were computed using the formulas in Anger 1967, vol. 1. Academic Press Inc.

| System | Full-body | Brain | Small-animal |
|---|---|---|---|
| Reconstruction diameter $D_{Rec}$ (cm) | 54.20 | 26.74 | 5.42 |
| Collimator bore diameter $D_{bore}$ (cm) | 62.58 | 30.88 | 6.25 |
| Collimator thickness T (cm) | 4.00 | 1.98 | 0.40 |
| Hole width d (mm) | 1.42 | 0.68 | 0.1 |
| Septal thickness t (mm) | 0.12 | 0.08 | 0.054 |
| Maximum transaxial penetration (%) | 1.5 | 5.9 | 5.0 |
| Detector resolution (mm) | 3 | 1.5 | 0.3 |
| Target resolution at the center of the FOV (mm) | 13.1 | 6.39 | 1.05 |
| Number of sectors per slice $N_s$ | 3 | 3 | 3 |
| Number of holes per sector $N_h$ | 352 | 352 | 352 |
| Number of slices N (# groups × # slices per group) | 40 × 8 | 40 × 2 | 40 × 8 |
| Angular increment between subsets | 3° | 3° | 3° |
| System axial length L (cm) | 49.28 | 6.08 | 4.93 |

Chapter Radioisotope Cameras, p 485-552. For the full-body system, it was chosen that the system parameters were similar to a modern commercial full-body SPECT system: the GE Discovery NM/CT 670, with its low energy/high resolution parallelhole collimator. In particular, the transaxial reconstruction FOV and the target resolution at the center of the image space are very similar in both systems. The brain and small-animal systems were scaled down such that the size of the reconstruction FOV would be larger than the average size of a human head and a mouse, respectively. For the brain system, this resulted in a scaling factor of roughly 2, and for the small animal system a factor of 10. However, the ratio between the septal thickness t and the hole width d needed to be increased to keep the septal penetration under 5%.

The standard sampling for rotating parallel-hole systems was according to 120 uniformly spaced angles over 360° and since there were 3 sectors of parallel-holes per collimator slice this corresponds to having 40 groups of slices rotated by 3° from each other. This should allow to achieve a sufficient angular sampling of the radiation source by stepping it through the collimator with an incremental translation equal to the thickness of a group of identical collimator slices. In the full-body and small-animal systems it was chosen to have 8 slices per group (oriented in the same direction), in order to reduce the number of steps of the scanning protocol; in the brain system, however, there are only 2 slices per group in order to allow the entire brain to go through the scanner without the shoulders going in, since they would not fit inside the collimator bore axis alone.

The system thus gives three sampling directions per slice and allows reconstruction of 75% of the transaxial area of the bore, and is approximately equivalent, in terms of the resulting sonogram, to a rotating parallel-hole SPECT system.

Simulations have shown that this new type of stationary SPECT system presents particular advantages that can be useful in many practical situations. Firstly, one of the most likely uses of such a system would be in SPECT-MR scanners, due to its very efficient use of space.

Secondly, it allows for very compact clinical and preclinical systems, therefore saving both space and material costs. Thirdly, this new type of collimator can easily be placed in already existing SPECT scanners to replace other collimators, since it only requires longitudinal movement of the patient bed, thereby making it cheap and practical to use. Lastly, it could allow us to build the first full-body human stationary SPECT scanner.

The invention claimed is:

1. A collimator for a SPECT system, the collimator being configured for absorbing and collimating gamma rays emitted by a radiation source within a field of view of the collimator, said collimator having an alignment direction for directing along a longitudinal axis of a measuring cavity of the SPECT system, said collimator comprising at least one collimator body formed as a continuous block of radiation absorbing material, the collimator body comprising a
plurality of apertures, the plurality of apertures being arranged in a plurality of groups separated from each other in said alignment direction,
wherein the apertures of each group are oriented such as to define at least one projection view along a corresponding at least one projection direction,
and wherein the plurality of said projection directions corresponding to each and every of said plurality of groups cover an angular range sufficiently large for sufficient image information for artifact-free reconstruction.

2. The collimator according to claim 1, wherein the projection view(s) of at least two different groups of apertures correspond with views on different positions along the alignment direction.

3. The collimator according to claim 1, wherein the apertures of each group are oriented so that each at least one projection direction is orthogonal to said alignment direction.

4. The collimator according to claim 1, wherein the plurality of groups comprise rows of apertures, each row of apertures being aligned on a corresponding plane.

5. The collimator according to claim 1, wherein each aperture within each group of apertures is parallel to all other apertures in said group.

6. The collimator according to claim 1, wherein the apertures of each group are oriented such as to define a number N larger than 1 of projection views along a corresponding number N of projection directions, each pair of said projection directions within the same group forming an angle being an integer multiple of 180/N degrees or 360/N degrees.

7. The collimator according to claim 1, wherein said plurality of apertures comprises pinholes, parallel holes or fanbeam holes.

8. The collimator according to claim 1, wherein said collimator has a cross-section perpendicular to the alignment direction having a circular shape, an elliptical shape, an oval shape or a polygonal shape.

9. The collimator according to claim 1, wherein said collimator is fabricated of a radiation-absorbing material comprising a heavy metal or an alloy thereof.

10. The collimator according to claim 1, wherein said plurality of apertures are obtained by a metal additive manufacturing technique.

11. The collimator according to claim 1, wherein the collimator is adapted in shape to fit between an at least one detector module and the measuring cavity of the SPECT system.

12. A SPECT system comprising:
a measuring cavity having a longitudinal axis,
a collimator according to claim 1 having its alignment direction aligned to said longitudinal axis,
a radiation detection means configured for receiving radiation passing through the collimator and for outputting a signal representative of the received radiation as function of spatial position, and
an actuation means configured for translating a radiation source through said measuring cavity along the longitudinal axis while imaging the radiation source.

13. The SPECT system according to claim 12, wherein said collimator and said radiation detection means are mechanically connected to a frame for maintaining said collimator and said radiation detection means stationary while imaging the radiation source.

14. Use of a SPECT system according to claim 13 for imaging a gamma-radiation emitting object.

15. Use of a SPECT system according to claim 12 for imaging a gamma-radiation emitting object.

* * * * *